United States Patent
Thorud et al.

[11] Patent Number: 6,019,779
[45] Date of Patent: Feb. 1, 2000

[54] MULTI-FILAR COIL MEDICAL STENT

[75] Inventors: Michael S. Thorud, Chanhassen; Richard C. Gunderson, Maple Grove, both of Minn.

[73] Assignee: Intratherapeutics Inc., St. Paul, Minn.

[21] Appl. No.: 09/169,246

[22] Filed: Oct. 9, 1998

[51] Int. Cl.[7] .......................... A61M 29/00; A61M 5/00
[52] U.S. Cl. .............................. 606/198; 623/1; 623/12
[58] Field of Search .............................. 606/1, 108, 194, 606/198, 200; 623/1, 12

[56] References Cited

U.S. PATENT DOCUMENTS

| | | |
|---|---|---|
| 4,553,545 | 11/1985 | Maass et al. . |
| 4,649,922 | 3/1987 | Wiktor . |
| 4,760,849 | 8/1988 | Kropf . |
| 4,886,062 | 12/1989 | Wiktor . |
| 5,147,370 | 9/1992 | McNamara et al. . |
| 5,201,901 | 4/1993 | Harada et al. . |
| 5,246,445 | 9/1993 | Yachia et al. . |
| 5,342,387 | 8/1994 | Summers . |
| 5,372,600 | 12/1994 | Beyar et al. . |
| 5,441,516 | 8/1995 | Wang et al. . |
| 5,449,372 | 9/1995 | Schmaltz et al. . |
| 5,556,413 | 9/1996 | Lam . |
| 5,597,378 | 1/1997 | Jervis . |
| 5,607,445 | 3/1997 | Summers . |
| 5,749,919 | 5/1998 | Blanc ........................................ 606/198 |
| 5,772,668 | 6/1998 | Summers et al. . |
| 5,797,952 | 8/1998 | Klein . |
| 5,843,168 | 12/1998 | Dang ........................................ 606/198 |

*Primary Examiner*—Michael Buiz
*Assistant Examiner*—William Lewis
*Attorney, Agent, or Firm*—Merchant & Gould P.C.

[57] ABSTRACT

Multi-filar, open and closed coil, tubular medical stents that are introduced to a site in a body lumen and released to expand at the site to provide a passageway through the stent lumen are disclosed. Each stent filar is a coil wound in substantially the same pitch through the majority of its length between the ends thereof. The coils are attached together at least at one coil end to form an end of the stent and wound in an interleaved manner such that the adjacent coils are substantially evenly spaced apart or in close contact in the released state and do not cross over one another. In one open coil stent embodiment, both ends of each coil are attached in respective first and second common attachment junctions, and the resulting coils have relatively even predetermined spacing between adjacent coil turns through the majority of the length of the stent between the first and last coil turns when the stent is released. Preferably, the first and second stent ends are formed by attaching the coil ends in common, and the stent ends are squared by decreasing the pitch of the first coil turn extending from the stent end such that the spacing of the stent end from the adjacent coil is reduced from the predetermined spacing. Additionally, multi-filar closed coil stent embodiments are disclosed having only one end of each coil attached in common and adjacent coil turns in substantial mutual and overlying contact in the restrained state during implantation and non-overlying contact in the released state. Preferably each common attachment junction of attached coil ends and each free coil end is formed into an enlarged stent end in at least one dimension for ease of attachment to and release from a stent delivery catheter. The common attachment junction can be snared or grasped by a stent retrieval system and retracted from the body lumen.

27 Claims, 5 Drawing Sheets

MULTI-FILAR COIL MEDICAL STENT

FIELD OF THE INVENTION

The present invention relates to tubular stents introduced to a site in a body vessel, duct or tract or other body lumen to provide a passageway through the stent lumen, and more particularly to a multi-filar coil stent and method of fabrication and implantation thereof.

BACKGROUND OF THE INVENTION

Surgical and other medical procedures are often undertaken that involve delivery and implantation of tubular stents or grafts within organs, cavities or body lumens including blood vessels, urinary tracts, esophageal tracts, respiratory tracts, bile ducts, and colo-rectal tracts, that function to maintain a lumen for passage of body fluids or blood therethrough. Such stents are employed typically to widen or maintain the width of such a body lumen where an obstruction, injury or disease process threatens to close it.

For example, percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.035 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to dilate. The dilatation of the occlusion, however, can form flaps, fissures and dissections which threaten re-closure of the dilated vessel or even perforations in the vessel wall after the balloon catheter is deflated and removed. Implantation of a stent can provide support or "scaffolding" for such flaps and dissections and thereby prevent re-closure of the vessel or provide a patch repair for a perforated vessel wall until corrective surgery can be performed. It has also been shown that the use of intravascular stents can measurably decrease the incidence of a later restenosis after angioplasty thereby reducing the likelihood that a secondary angioplasty procedure or a surgical bypass operation will be necessary.

Intravascular stents and grafts can also be used to repair aneurysms, to support artificial vessels as liners of blood vessels or to repair dissections of blood vessels. The vascular passageways maintained open by stents range in diameter from small coronary vessels of 3 mm or less to 28 mm in the aortic vessel. Moreover, as noted at the outset, suitably sized stents have been proposed or clinically employed to maintain the patency of other body lumens, including the vas deferens, ducts of the gallbladder, prostate gland, trachea bronchus and liver.

A wide variety of stent designs have been proposed and/or clinically employed in such body lumens including solid tubular metal or plastic tubes, coiled wire stents, mesh stents, fabric grafts, and the like, that may be either permanently or temporarily implanted. The stent is typically delivered to the site of implantation in a small diameter, compressed state and then radially expanded to an expanded state against the body vessel wall. Depending upon the design, the stent can be made to be radially self-expanding in situ when released from a delivery catheter or the like or expandable by the use of an expansion device, e.g., a balloon catheter, operated from outside the patient's body. A variety of expandable stents that employ an expanding balloon, including typical single coil wire expandable from a delivered diameter to an expanded diameter are disclosed in U.S. Pat. No. 4,886,062 to Wiktor and in U.S. Pat. No. 5,201,901 to Harada et al.

Self-expanding, single coil, wire stents are disclosed in commonly assigned U.S. Pat. Nos. 5,372,600 to Beyar et al. and 5,246,445 to Yachia et al and in U.S. Pat. No. 5,797,952 to Klein. Such single coil wire stents are characterized as "open coils" having substantial apparent spacing between adjacent coil turns when in the expanded state or as "closed coils" having insubstantial spacing between or actual contact of adjacent coil turns. Single filar, open coil, wire stents that range from 15 mm to 150 mm in length and 2 mm to 12 mm in diameter when released and self-expanded in situ have been sold or proposed by the assignee of the present invention in various CardioCoil™ and VascuCoil™ models for coronary and peripheral vascular implantation. Further single, closed coil, wire stents that range from 40 mm to 150 mm in length and 6 mm to 30 mm in diameter when released and self-expanded in situ have been sold or proposed by the assignee of the present invention in various EndoCoil™, EsophoCoil™, CoRectCoil™, UroCoil™, and ProstaCoil™ models for implantation in the bile duct, esophagus, colorectal tract and urinary tract.

Use of certain of these stents is described by Beyar et al. in *Cath. Cardiovasc Diag.*, 32:162–170 (1994). In each case, the coil stent is delivered by winding it down into a smaller diameter and fixing it onto a stent delivery catheter as also explained in the above-referenced '445 and '600 patents. When the stent is positioned at the desired site, the ends of the stent are released from the catheter, and the single filar coiled wire stent self-expands by its spring force to the specified released stent diameter and length dimensions.

These single filar stents are formed of a single filar wire having a circular cross-section or a rectangular or "ribbon shaped" cross-section (although other cross-section shapes are suggested in the above-referenced '600 patent) terminating with enlarged "ball tips" at the wire ends. The ribbon shaped wire is preferred because it can be formed of many desirable materials, e.g., superelastic or pseudoelastic alloys such as disclosed in U.S. Pat. No. 5,597,378 to Jervis, and results in a "low profile" or thin stent scaffolding that depends on the ribbon shaped thickness. In addition, ribbon shaped wire can achieve stent strength equivalent to stents of the same stent diameter and coil pitch made of round wire but employing a thickness that is thinner than the round wire diameter, thus yielding smaller strains when wound down. The ribbon shaped wire can be therefore wound down to a smaller diameter about a stent delivery catheter without exceeding its strain limit and suffering plastic deformation than the comparable circular cross section wire. If the strain is too large, the material will experience plastic deformation to such an extent that the stent will not recover to the intended length and diameter dimensions following release and deployment.

A self-expanding, double spiral coil, wire stent and delivery catheter are disclosed in U.S. Pat. No. 5,772,668 to Summers et al. The double spiral coil is formed of a continuous loop having a pair of parallel legs that are joined together at each end of the legs by U-shaped, semicircular, end cusps. The legs formed into the continuous loop are wound into a coil of constant pitch and common diameter between the opposite end cusps. In this way, each leg remains in parallel to the other leg, and in some instances the end cusps project away from one another and in the axial direction of the coil. The inner diameters of the semicircular cusps define the spacing between the legs of the loop.

The double spiral coil stent is wound about the delivery catheter in the reduced diameter so that the adjacent legs do not overlap one another. In one embodiment, the distal ends of retention wires that extend through the hollow lumens of the delivery catheter are extended through the interior loops of the end cusps to retain the double spiral coil stent compressed about the catheter surface during introduction to the selected site. The retention wires are retracted from the interior loops to release the double spiral coil stent, allowing it to expand at the implantation site. In other embodiments, the end cusps are extended axially to hook the U-shaped cusp ends over radially projecting pins or cams, and the stent delivery catheter is manipulated to release the cusp ends. In this case, the stent ends are stressed axially so that the axial spring force applied through the cusp ends to cams overcomes the radial spring force that would cause the stent ends to release from the cams.

The use of the end cusps and legs constructed in this manner and these retention mechanisms require that the end cusps and short sections of the legs coupled thereto to be bent or twisted to fit the retention mechanisms of the stent delivery catheter through the cusp ends during implantation. The stents of the '668 patent are described as being formed in several ways, but the depicted stents appear to be formed of substantially circular cross-section wire that is first formed into a loop defining the two legs and end cusps described above and then wound into a stent coil. The deformations of the stent ends to be attached to the retention and release mechanisms of the stent delivery catheter is best accomplished when the stent cross-section is substantially circular because it is difficult to bend ribbon shaped wire against its width direction. Thus, the strain resistance and stent profile advantages of ribbon shaped wire cannot be realized using the loop defining the two legs and end cusps described above.

Moreover, use of the end cusps to couple the legs together and the constant spacing between the two parallel legs limits the distance that the legs can be spaced apart in the preformed loop that is wound to form the double coil stent of the '668 patent. If the cusp end diameter is increased to accommodate a greater spacing between the legs, then the projections of the end cusps in the direction of the stent coil axis is increased in severity. Therefore, the leg spacing defined by the end cusp diameters either limits the pitch of the spiral dual coil stent to maintain a constant distance or spacing between the wire coil turns or causes the resulting adjacent stent coil turns to have a spacing that is wider than the spacing between the parallel legs as shown in the figures of the '668 patent. As a result, the uneven, alternating wide and narrow spacing of adjacent coil turns causes the support or "scaffolding" of the body lumen to be uneven.

Finally, it is frequently desirable to be able to retrieve a deployed and expanded stent if it is not deployed optimally. The end cusps of the double spiral coil stent of the '668 patent would be difficult to snag to retrieve it and retract it into the lumen of a catheter.

SUMMARY OF THE INVENTION

It is therefore an object of the present invention to provide a multi-filar, open coil or closed coil, stent that provides for substantially even spacing between adjacent coil turns when expanded, thereby providing good coverage while realizing greater lateral stability of the stent from the resulting pitch.

It is a further separate object of the invention to square the free ends of such multi-filar, open coil stents when in the expanded state.

It is still a further separate object of the invention to facilitate the retrieval of such multi-filar stents that are released into the expanded state in situ.

It is another separate object of the invention to provide a multi-filar, open coil stent wherein in the constrained or restrained state, the stent is wound about the stent delivery catheter such that the stent diameter is reduced while the restrained stent length is substantially the same as the expanded stent length to allow access deeper into body lumens and more accurate placement of the stent when it is released.

It is still another separate object of the present invention to provide attachment structure at the ends of the multi-filar coil stents for effecting attachment with a stent delivery catheter.

It is yet a further separate object of the invention to provide a multi-filar, closed coil stent that can be decreased in stent length when wound down to a reduced state stent diameter and mounted to a stent delivery catheter.

These and other objects of the present invention are realized separately or in various combinations in multi-filar stents where each filar is a coil wound in substantially the same pitch through the majority of its length between the ends thereof. The coils are interleaved with one another so that they do not cross over one another when expanded into the unrestrained, released state. The number of coils is preferably two or three or more, and the coils are attached together at least at one coil end to form an end of the stent and wound in the interleaved manner such that the adjacent coils are substantially evenly spaced apart a predetermined coil spacing in the released state. In open coil embodiments, the stent ends formed by attaching the coil ends in common are squared by decreasing the pitch of the first coil wire turn extending from the stent end such that the spacing of the stent end from the adjacent coil is reduced from the predetermined spacing.

In one embodiment, both ends of each coil are attached in respective first and second common attachment junctions, and the resulting multi-filar stent forms an open coil stent having relatively even predetermined coil spacing between adjacent coil turns through the majority of the length of the stent between the first and last coil turns when the stent is released. In the constrained or restrained state, the stent is wound about the stent delivery catheter such that the stent diameter is reduced while the restrained stent length is substantially the same as the released stent length which allows access deeper into body lumens and more accurate placement of the stent when it is released.

In another embodiment, only one end of each coil is attached in common, and preferably, a closed coil stent is formed having adjacent coil turns in substantial mutual contact in both the restrained state during implantation and in the expanded state. In the constrained state, the adjacent coil turns are wound in an overlapping manner about the delivery catheter which also shortens the constrained stent length from the length that it would otherwise assume if not overlapped.

Preferably each common attachment junction of attached coil ends is formed into an enlarged stent end for ease of attachment to and release from the delivery catheter using attachment and release mechanisms of the delivery catheter that loop about the common attachment junction. Moreover, the enlarged stent end provides a mechanism that can be snagged by a stent retrieval snare or grasper introduced through a stent retrieval catheter to a point adjacent to or encompassing the enlarged stent end and drawn or retracted into the catheter lumen.

The adjacent turns of the plurality of interleaved coils contact the body lumen wall at relatively closer spacing than the spacing between individual turns of each coil. In this way, the pitch of each coil is increased in proportion to the number of coils; for example, the coils of a bi-filar stent have twice the pitch as a single coil stent having the same coil spacing and stent diameter. The increased winding pitch of each coil on the multi-filar stent of the present invention increases lateral stability of the stent between the first and second stent ends in comparison to a single coil stent having the same coil spacing, stent diameter and length due to the relatively greater pitch and turn spacing between turns of each coil than the spacing between adjacent turns of the plurality of coils.

The coil filars of the multi-filar stent embodiments of the present invention are preferably formed in a rectangular cross-section of a nickel-titanium, superelastic, shape memory, Nitinol® alloy but could be made of other biocompatible materials, e.g., stainless steel, Elgiloy® alloy, polymers, or bio-absorbable compounds. Moreover, they can be coated with other metals or with polymers, drugs or radioactive compounds or covered by an expandable tube of a bio-compatible elastomer, e.g., silicone rubber or a folded Dacron® fabric tube, that expands or straightens out as the stent diameter and length increases to form a fluid impervious or pervious graft.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the invention will become apparent from the following detailed description of the preferred embodiments of the invention, in which.

DETAILED DESCRIPTION OF THE PREFERRED EMBODIMENTS OF THE INVENTION

The present invention can be implemented in a multi-filar stent where each filar is a coil wound in substantially the same pitch through the majority of its length between the ends thereof, except for the final coil turn approaching an end, and the coils are interleaved with one another so that they do not cross over one another. The number of coils is preferably two or three or more, and bi-filar and tri-filar coil stents are described and depicted in the drawing figures as preferred embodiments of the present invention.

Figure 1:
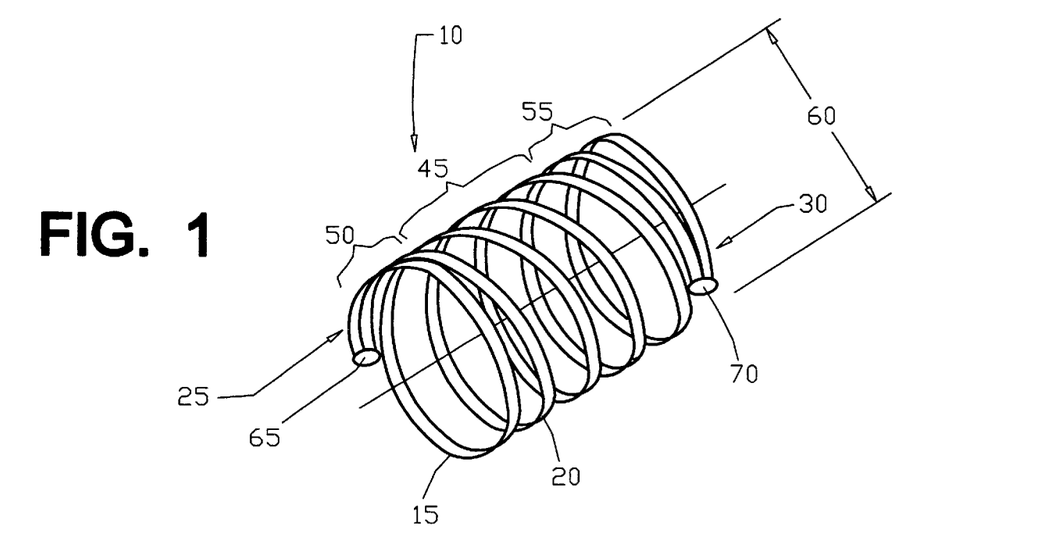
FIG. 1 is a perspective view of a bi-filar open coil stent having the coil ends at both stent ends attached together in accordance with the present invention.
Figure 2:
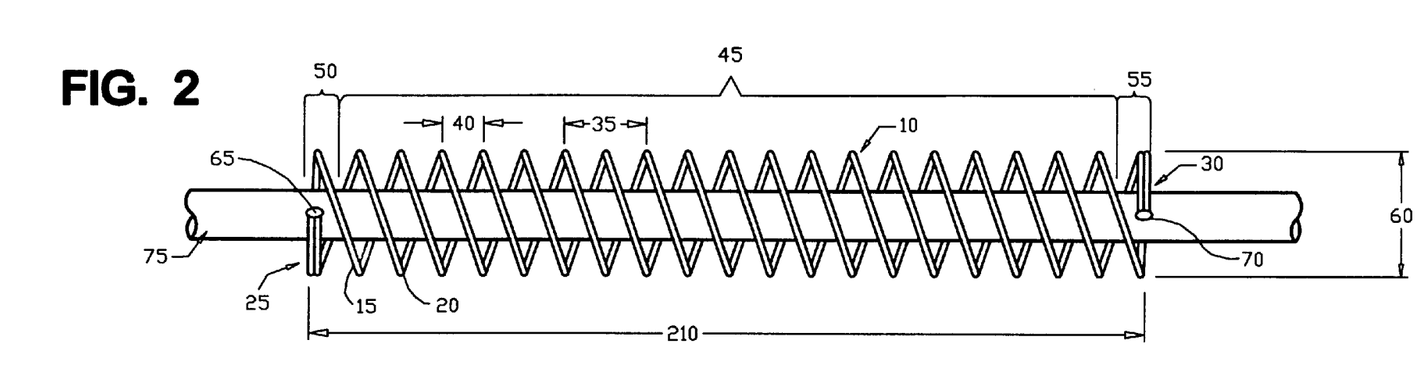
FIG. 2 is a side view of a bi-filar open coil stent of the type depicted in FIG. 1 in the expanded state in relation to a stent delivery catheter.
Figure 3:
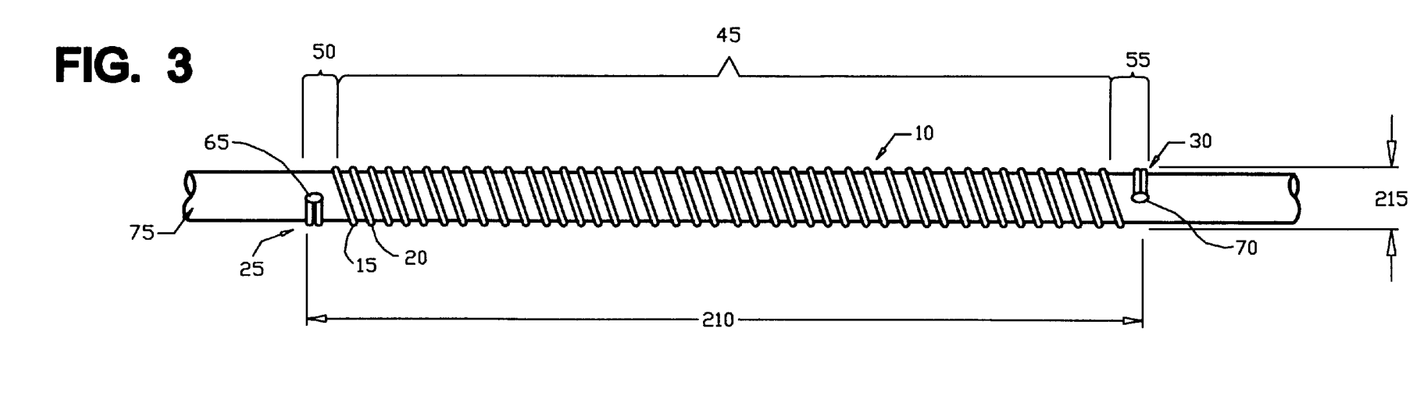
FIG. 3 is a side view of the bi-filar open coil stent of the type depicted in FIG. 1 in the restrained state attached to a stent delivery catheter.

FIGS. 1–3 show a bi-filar open coil stent 10 formed in accordance with the present invention of first and second coils 15 and 20 which are attached together at attachment junctions of the coil ends to form first or proximal and second or distal, stent ends 25 and 30, respectively. The first and second coils 15 and 20 are preferably formed of a nickel-titanium, superelastic, shape memory, Nitinol® alloy having a rectangular or ribbon shaped cross-section.

In the released state depicted in FIGS. 1 and 2, each coil 15 and 20 is wound in substantially the same pitch 35 and spacing 40 through the major length 45 between the first coil turns 50 and 55 approaching stent ends 25 and 30. The first and second coils 15 and 20 are interleaved with one another so that they do not cross over one another and have substantially the same released outer diameter 60 when in the released state shown in FIGS. 1 and 2. It will be understood that their diameters can differ from one another or that the released outer diameter 60 can vary along the full stent length 210, e.g., by increasing toward one or both of the stent ends 25 and 30 or toward the center.

The stent tails or ends 25 and 30 formed by attaching the coil ends in common are squared by decreasing the pitch of the first or proximal and second or distal (arbitrarily designated) coil turns 50 and 55 extending from the stent ends 25 and 30 from the coil pitch 35. The spacing of the first and second stent ends 25 and 30 from the adjacent coil is thereby reduced from the relatively uniform predetermined spacing 40, and the first and second stent ends 25 and 30 are more tubular or squared.

The proximal ends of the first coil 15 and the second coil 20 are attached together in a side by side or overlapping manner to form a proximal enlarged ball tip 65 and the distal ends of the first and second coils 25 and 30 are attached together to form a distal enlarged ball tip 70. The first and second enlarged ball tips 65 and 70 can be employed during the delivery and implantation of the stent 10 to a site in a body lumen or employed in removal of the deployed stent. Each of the ball tips 65 and 70 are preferably ovaloid or football shaped, whereby they are about the same length as the widths of the ribbon shaped first and second coils 25 and 30 but are thicker than the thickness of the first and second coils 25 and 30.

Figure 4:
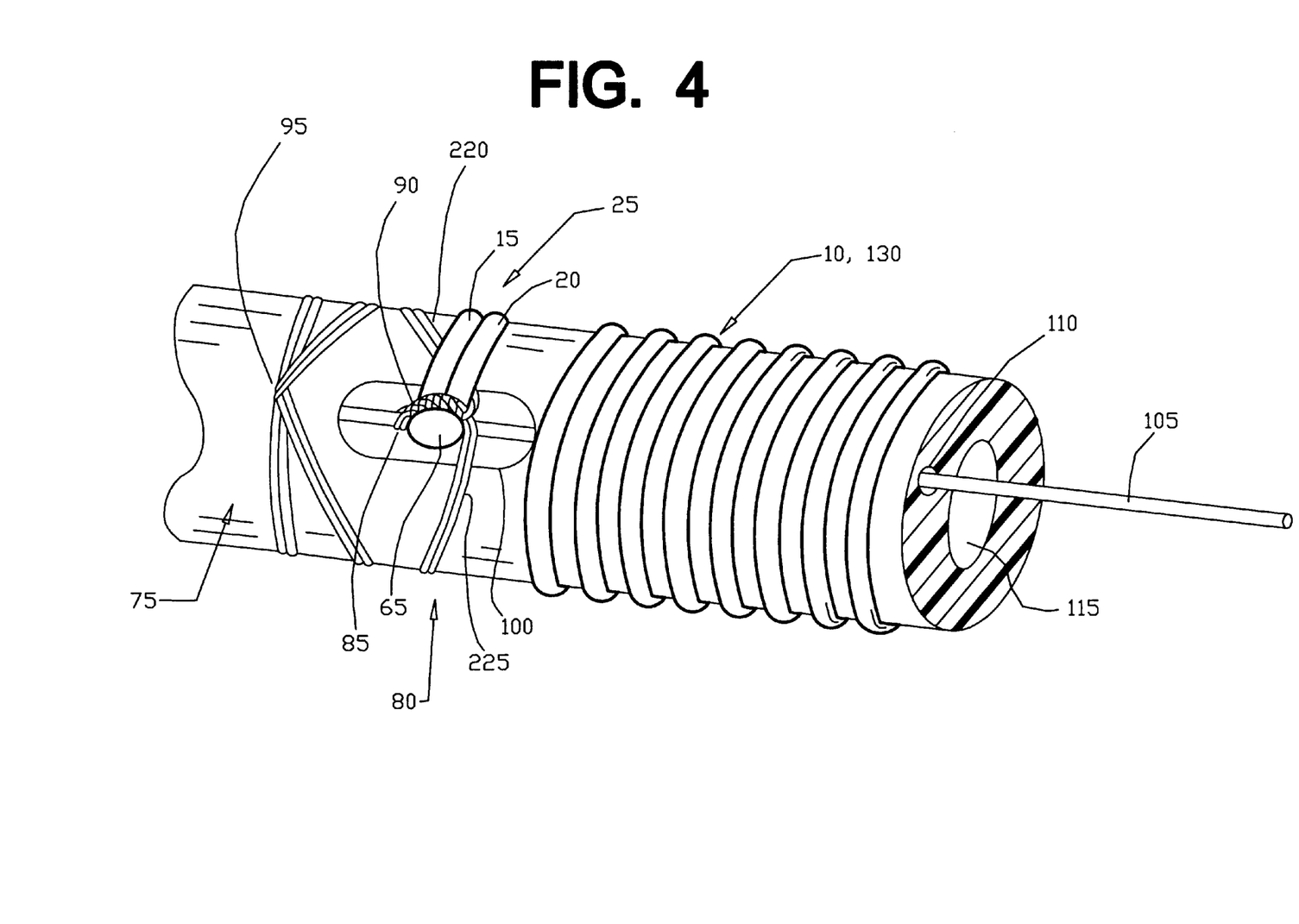
FIG. 4 is a partial perspective view of the bi-filar open coil stent of the type depicted in FIG. 1 in the restrained state wound about a stent delivery catheter and showing how a stent end can be attached to the stent delivery catheter.

FIGS. 3 and 4 depict the stent 10 in the restrained state, wherein the stent 10 is wound about the stent delivery catheter 75, thereby reducing the spacing 40 between adjacent coil turns such that the total stent length 210 remains about equal to that in the released state of FIG. 2. However, the restrained stent coil diameter 215 is reduced to about 10% to 90% of the released stent diameter 60, in a typical case.

In the exemplary stent delivery system depicted in part in FIG. 4, the respective first and second stent ends 25 and 30 are restrained by respective proximal and distal restraining means near the stent delivery catheter distal end. Only the proximal restraining means 80 is depicted that engages the proximal stent end 25 and with a fixation wire 105 traversing a fixation wire lumen 110. It will be understood that the distal fixation means is configured and engages with the distal stent end 30 and the fixation wire 105 (or a separate fixation wire traversing a separate fixation wire lumen). The proximal and distal restraining means each comprise a paired suture loop 85 that loops around fixation wire 105 extending through the fixation wire lumen 110. This doubled suture loop 85 is then woven into a four strand suture braid 90 which extends out of proximal opening 100 in the side of the stent delivery catheter 75 that intersects the fixation wire lumen 110. The suture braid 90 passes over the external lateral surface of the stent end 25 adjacent to the ball tip 65 and then splits into two pairs of suture wraps 220 and 225 that wrap in opposite directions around the circumference of the stent delivery catheter 75 and are knotted on the back side (not shown) of the delivery catheter 75. The two pairs of suture wraps 220 and 225 continue in opposite directions around the delivery catheter 75 and are joined at the depicted suture knot 95. The two pairs of suture wraps are then wrapped around the circumference of the stent delivery catheter and are knotted and terminated on the back side thereof (not shown).

The tension of the suture braid 90 against the enlarged proximal ball tip 65 and the distal suture braid against the enlarged distal ball tip (or the separate ball tips described below with reference to FIG. 7) maintains the stent 10 in the restrained or reduced state stent length and diameter wrapped about the length of the stent delivery catheter 75 between the proximal and distal restraining means during the advancement of the stent delivery catheter to a desired site in a body lumen for release and deployment of the stent 10. This advancement can be effected over a previously advanced guidewire (not shown) extending through the primary stent delivery catheter lumen 115. Once the stent 10 is positioned, the fixation wire 105 (or fixation wires) is retracted proximally of the stent 10, releasing the suture loop 85, and the stent diameter and length and the spacing between adjacent coils expands to those dimensions shown in FIG. 1.

It will be understood that other stent delivery systems than the stent delivery system depicted in FIG. 4 that cooperate with the ball tips 65 and 70 can be employed in the placement of the stent 10. Such alternative stent delivery systems include those disclosed in the above-referenced '600 patent or are equivalent structures employed in the delivery of the above-referenced stents sold by the assignee of the present invention.

Figure 5:
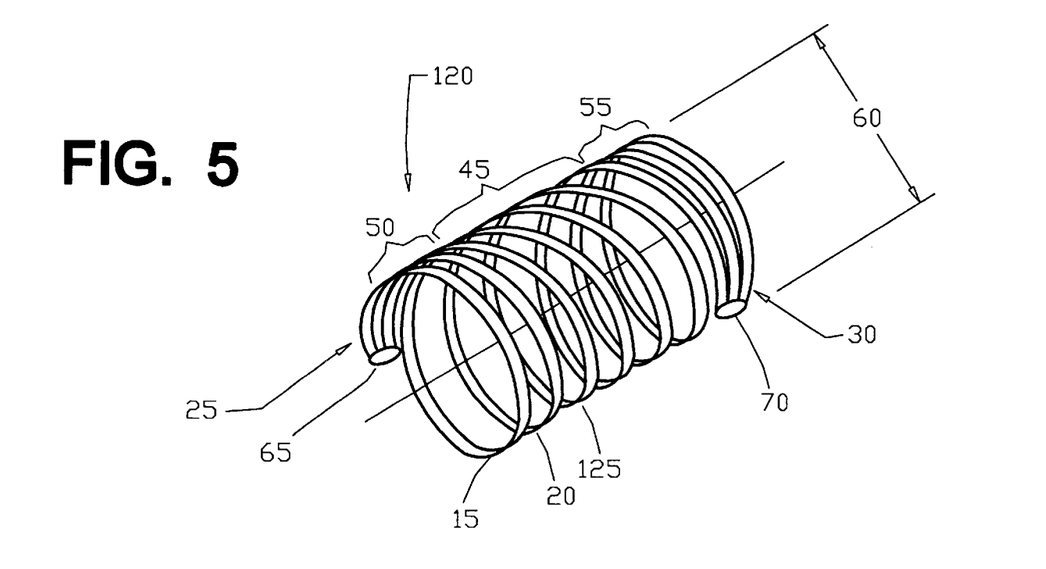
FIG. 5 is a perspective view of a tri-filar open coil stent having the coil ends at both stent ends attached together in accordance with the present invention.

FIG. 5 is a perspective view of a tri-filar open coil stent 120 having the coil ends at both stent ends 25 and 30 attached together in accordance with a further embodiment of the present invention. In this embodiment, a third coil 125 is interleaved with the first coil 15 and the second coil 20, and the stent otherwise is similar to the stent 10 and is deployed in the same manner as shown in FIG. 4 and described above.

Additional coils can be interleaved into multi-filar open coil stents of the types depicted in FIGS. 1–5. The overall stent length 210 can range from 10 mm to 200 mm, and the unrestrained stent diameter 60 can range from 2 mm to 30 mm. The coil spacing 40 between adjacent coils 15 and 20 or 15, 20 and 125 can be fairly wide or narrow in a range of 0 mm to 20 mm. Preferably, the coils 15, 20, 125 are formed in rectangular cross-section and from a shape memory material e.g., superelastic or pseudoelastic alloys such as disclosed in the above-referenced '378 patent in order to sustain tight wrapping and substantial reduction of the restrained stent outer diameter 215 about the stent delivery catheter 75 without substantial permanent deformation. In the bi-filar embodiment, the ribbon shaped, coil wire preferably has a thickness of about 0.15 mm to 0.40 mm and a width of about 0.30 mm to 5.00 mm.

Figure 6:
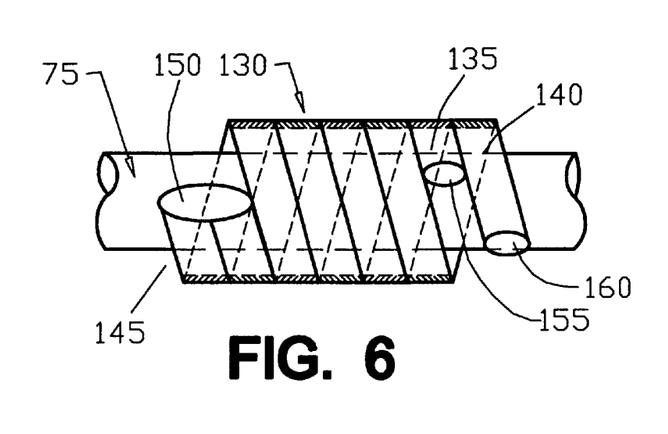
FIG. 6 is a side view of a bi-filar closed coil stent having the coil ends at only one stent end attached together in the expanded state in relation to a stent delivery catheter.
Figure 7:
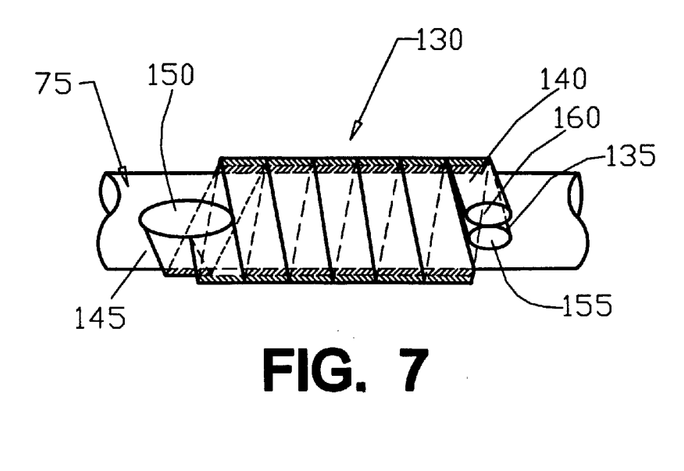
FIG. 7 is a side view of the bi-filar closed coil stent of the type depicted in FIG. 6 in the restrained state attached to a stent delivery catheter wherein the adjacent coils are stacked over one another.

The present invention is also implemented in further multi-filar closed coil stents wherein the coils of the stent are only connected together at one of the first and second stent ends so that the coils can be disposed side by side in the released state and be stacked over one another in the constrained or reduced state. FIGS. 6 and 7 show a bi-filar closed coil stent 130 formed of first and second coils 135 and 140 having rectangular cross-section. The coil ends at the proximal stent end 145, for example, are attached together and an enlarged ball tip 150 is formed at the attachment junction. Separate distal ball tips 155 and 160 are formed at the other or distal ends of the first and second coils 135 and 140. The separate ball tips 155 and 160 are not joined together to allow for the relative shifting of the two filars when stacked, since the outer filar is at a greater circumference.

FIG. 7 is a side view of the bi-filar closed coil stent 130 in the restrained state attached to a stent delivery catheter 75 wherein the adjacent coils 135 and 140 are stacked over one another. In this way, for implantation, the reduced state stent diameter is decreased from the expanded state stent diameter and the reduced state stent length is smaller than it otherwise would be if the coils 135 and 140 are not stacked upon one another. The stent ends are restrained by proximal restraining means 80 and distal restraining means in the manner shown in FIG. 4, for example. The distal ball tips 155 and 160 can be restrained by a single distal restraining means having a single suture braid like the proximal restraining means 80 depicted in FIG. 4 or having separate similar suture braids engaging the coil distal ends against the separate distal ball tips 155 and 160.

Figure 8:
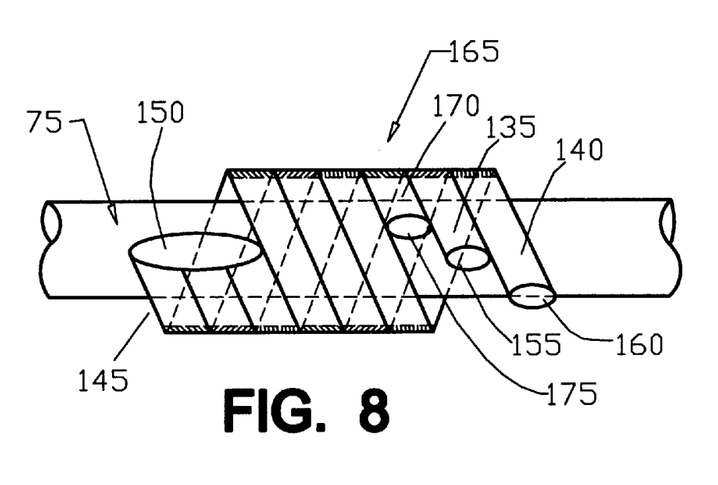
FIG. 8 is a side view of a tri-filar closed coil stent having the coil ends at only one stent end attached together in the expanded state in relation to a stent delivery catheter.
Figure 9:
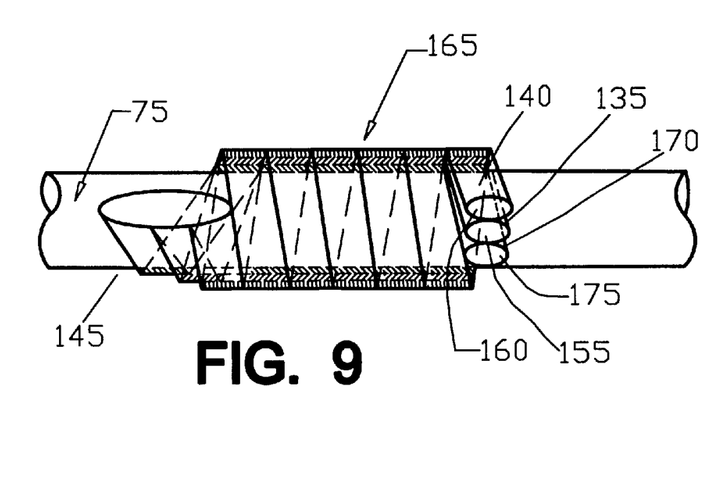
FIG. 9 is a side view of the tri-filar closed coil stent of the type depicted in FIG. 6 in the restrained state attached to a stent delivery catheter wherein the adjacent coils are stacked over one another.

Similarly, FIGS. 8 and 9 depict a tri-filar closed coil stent 165 having a third flat coil 170 interleaved with the first coil 135 and the second coil 140. The flat coil 170 is attached to the proximal enlarged ball tip 150 and terminates with a further ball tip 175 at its free distal end. The tri-filar stent 165 is otherwise similar to the bi-filar stent 130 and is deployed in the same manner as shown in FIG. 4 and described above.

The depiction in FIGS. 6–9 of these multi-filar closed coil stents is schematic and exaggerated for effect. The ribbon shaped cross section coils 135, 140 and 170 can be narrower and formed so that their edges contact one another in the deployed stent state as shown in FIGS. 6 and 8 or so that there is a slight spacing between their adjacent coil turn edges. Alternatively, the cross-section of each coil 135, 140, 170 can be in a stepped shape so that the adjacent coil turn edges can partially overlap one another in the deployed or released states of FIGS. 6 and 8.

In addition, the coils of all of the stent embodiments of FIGS. 1–9 can be coated with other metals, drugs, polymers or radioactive compounds or covered by an expandable tube of a bio-compatible elastomer, e.g., an impervious silicone rubber tube sheeting or a folded Dacron® fabric tube, that expands or unfolds and straightens out as the stent diameter and length increases to form a fluid impervious or pervious graft.

Figure 10:
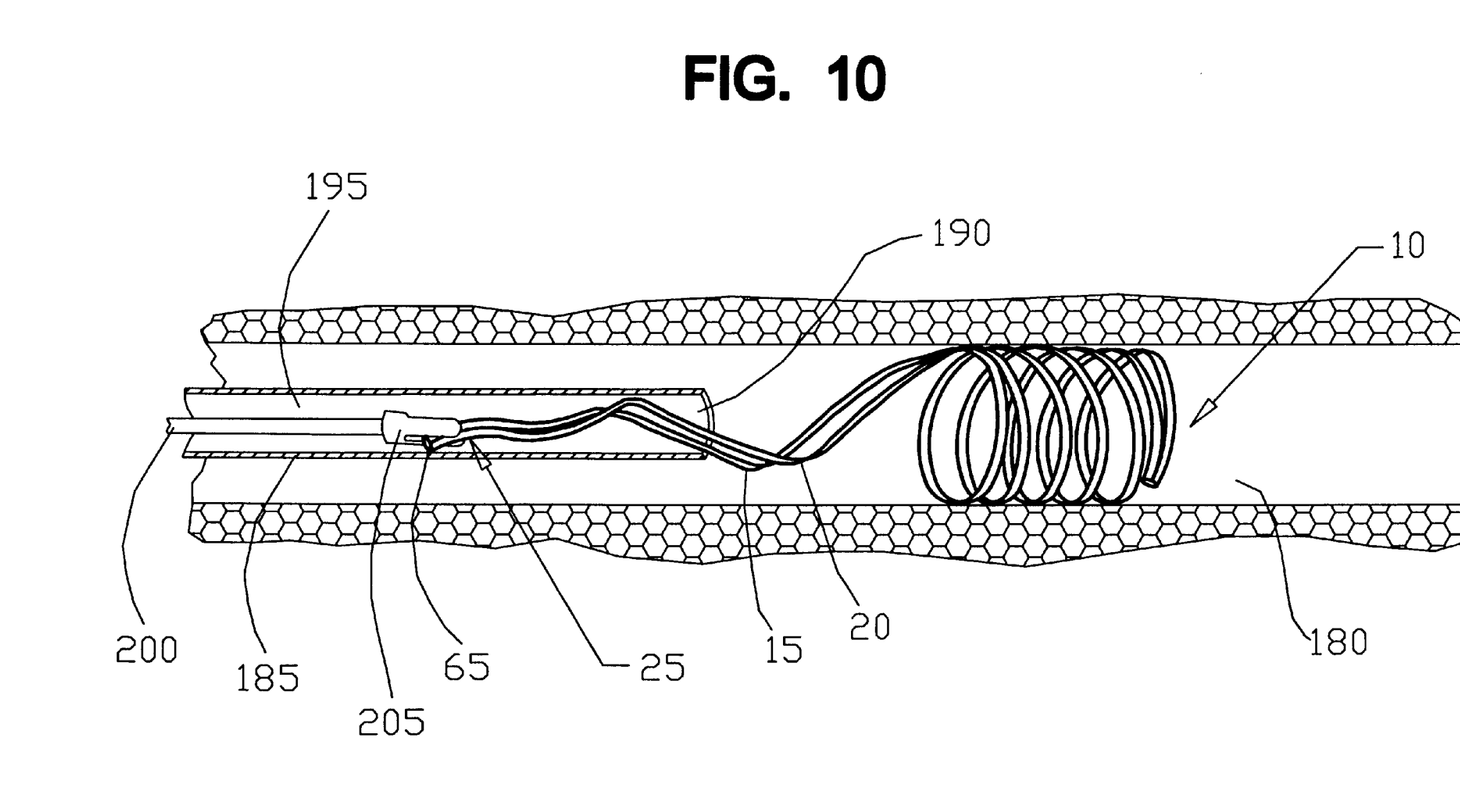
FIG. 10 is a side view of a manner of grasping and removing a stent released into a body lumen in accordance with the present invention.

FIG. 10 is a side view of a manner of grasping and removing the above-described stent embodiments and equivalents thereto, e.g. bi-filar open coil stent 10 for example, after it has been released into a body lumen 180 using the stent delivery system. Using endoscopy, a stent retrieval catheter 185 is introduced to the site, typically proximal to the proximal end of the stent 10. A stent retrieval tool 200 having a snare loop or grasper 205 is introduced through the stent retrieval catheter lumen 195 and extended distally from lumen distal end opening 190. The illustrated grasper 205 is expanded and fitted over the coils 15 and 20 adjacent to or encompassing the proximal enlarged ball tip 65 and then tightened against the proximal stent end 25 to grasp it. The stent retrieval tool 200 is then retracted to pull stent 10 proximally through the stent retrieval catheter lumen 195. The coils of the stent 10 are resilient enough to unwind and be drawn through the stent retrieval catheter lumen 195 without damaging the tissue wall of the body lumen 180. This system and method can be employed to retrieve any of the stents of the present invention from the enlarged ball tip at the common attachment junction of the coils of the stent.

The preferred embodiments of the invention are described above as comprising self-expanding multi-filar open and closed coil stents that expand from a constrained or restrained stent diameter to a released stent diameter with or without a change in stent length within the body lumen effected by the superelastic nature of the coil material employed. It will be understood that the principles of the present invention can be applied to stents of similar configuration but of different materials that are expanded by an expansion mechanism. Moreover, it will be understood that the self-expansion of the multi-filar open and closed coil stents when released into the body lumen can be effected by a state transition caused by exposure to the body temperature in a manner described, for example, in the above-referenced '952 and '378 patents.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

PARTS LIST FOR FIGS. 1–10 bi-filar open coil stent 10
first coil 15
second coil 20
first or proximal stent end 25
second or distal stent end 30
coil pitch 35
coil spacing 40
stent major length 45
proximal coil turn 50
distal coil turn 55
released stent coil outer diameter 60
proximal enlarged ball tip 65
distal enlarged ball tip 70
stent delivery catheter 75
proximal restraining means 80
suture loop 85
suture braid 90
suture knot 95
opening 100
fixation wire 105
fixation wire lumen 110
primary stent delivery catheter lumen 115
tri-filar open coil stent 120
third coil 125
bi-filar closed coil stent 130
first coil 135
second coil 140
proximal stent end 145
enlarged ball tip 150
ball tip 155
ball tip 160
tri-filar closed coil stent 165
third flat coil 170
ball tip 175
body lumen 180
stent retrieval catheter 185
lumen distal end opening 190
stent retrieval catheter lumen 195
stent retrieval tool 200
grasper 205
total stent length 210
restrained stent coil diameter 215
suture wrap 220
suture wrap 225

We claim:

1. An implantable multi-filar coil stent having a substantially tubular shape and an expanded stent length and expanded stent diameter in an expanded state adapted to be introduced, while reduced to a reduced stent diameter and stent length, to a site in a body lumen and implanted at the site at an expanded stent diameter and stent length in contact with the wall of the body lumen comprising:

a plurality of coils each having a pre-determined coil cross-section and extending for a predetermined length between a first coil end and a second coil end and each wound in a common winding direction and having a common winding pitch through an intermediate portion of the coil length intermediate the first and second coil ends with opposing turns of said coils being substantially parallel spaced-apart in said intermediate portion and with said coils being non-overlapping in said intermediate portion; and said first coil ends coupled together at a first stent end for cooperatively maintaining said plurality of coils in a multi-filar winding relationship providing the substantially tubular stent shape and maintaining substantially parallel spacing between adjacent turns of the plurality of coils through said intermediate portion and, at said first stent end, said winding pitch of said plurality coils respectively varied for said first ends of said coils to be angled toward one another in helical paths to a cuspless, first common junction point in side-by-side alignment.

2. The multi-filar coil stent of claim 1 further comprising a first enlarged tip at said first common junction point and having a cross-section exceeding, in at least one direction, the combined cross-section of the plurality of coils attached together at said first common junction point.

3. The multi-filar coil stent of any of claim 1, wherein said plurality of coils of said coil stent are formed with a rectangular cross-section.

4. The multi-filar coil stent of any of claim 1, wherein said coils of said coil stent have an elasticity allowing said coils to be wound under applied force to a restrained diameter on stent deployment means to allow for introduction of said coil stent to the site of implantation while reduced in diameter and to unwind from said restrained diameter and to resume substantially said expanded stent diameter when implanted at the site.

5. The multi-filar coil stent of any of claim 1, wherein said coils of said coil stent are formed of a superelastic metal alloy and have an elasticity allowing said coils to be wound under applied force to a restrained diameter of about 10% to 90% of the expanded stent diameter on stent deployment means to allow for introduction of said coil stent to the site of implantation while reduced in diameter and to unwind from said restrained diameter and to resume substantially said expanded stent diameter when implanted at the site.

6. The multi-filar coil stent of any of claim 1, wherein said coils of said coil stent have an elasticity allowing said coils to be wound under applied force to a restrained diameter and a restrained pitch on stent deployment means to allow for introduction of said coil stent to the site of implantation while reduced in diameter and having a reduced state stent length that is substantially the same as the expanded stent length and to unwind from said restrained diameter and to resume substantially said expanded stent diameter, pitch and stent length when implanted at the site.

7. The multi-filar coil stent of any of claim 1, wherein said plurality of coils have a common cross-section and said plurality of coils comprise two coils.

8. The multi-filar coil stent of any of claim 1, wherein said plurality of coils have a common cross-section and said plurality of coils comprise three coils.

9. The multi-filar coil stent of any of claim 1, wherein said coils of said coil stent are formed of a superelastic metal alloy and have an elasticity allowing said coils to be wound under applied force to a restrained diameter and a restrained pitch on stent deployment means to allow for introduction of said coil stent to the site of implantation while reduced in diameter and having a reduced state stent length that is substantially the same as the expanded stent length and to unwind from said restrained diameter and to resume substantially said expanded stent diameter, pitch and stent length when implanted at the site.

10. The multi-filar coil stent of any of claim 1, further comprising a tubular sheath of fluid pervious or impervious material fitted over said plurality of coils.

11. The multi-filar stent according to claim 1 wherein said second coil ends are coupled together at a second stent end with said winding pitch of said plurality coils respectively varied at said second coil ends for said second ends of said coils to be angled toward one another to a second cuspless, common junction point.

12. The multi-filar coil stent according to claim 11 further comprising a first enlarged tip at said first common junction point and having a cross-section exceeding, in at least one direction, the combined cross-section of the plurality of coils attached together at said first common junction point.

13. A system for implanting a tubular stent at a site in a body lumen at an expanded stent diameter and stent length in contact with the wall of the body lumen comprising:

a stent having a substantially tubular shape and an expanded stent length and expanded stent diameter in an expanded state formed of a plurality of coils each having a pre-determined coil cross-section and extending for a predetermined length between a first coil end and a second coil end and each wound in a common winding direction and having a common winding pitch through a substantial portion of the coil length intermediate the first and second coil ends, and with first end coupling means for coupling the plurality of first coil ends together at a first stent end and with second end coupling means for coupling the plurality of second coil ends together at a second stent end for cooperatively maintaining said plurality of coils in is an interleaved, multi-filar winding relationship providing the substantially tubular stent shape and maintaining substantially equal coil spacing between adjacent turns of the plurality of coils through a substantial portion of the lengths of the plurality of coils, said first end coupling means comprising a first enlarged tip attached to each of the first coil ends having a cross-section exceeding, in at least one direction, the combined cross-section of the plurality of coils attached together at the first stent end, and said second end coupling means comprising a second enlarged tip attached to each of the second coil ends, whereby the first coil ends are commonly coupled together and the second coil ends are commonly coupled together; and a a stent implantation catheter extending between proximal and distal ends and having a stent mounting and release mechanism for restraining said tubular stent wound around a distal end segment thereof and reduced to a reduced state stent diameter and stent length, said stent mounting and release mechanism further comprising:
first means for attaching the stent implantation catheter release mechanism around the first coil end and against the first enlarged tip;
second means for attaching the stent implantation catheter release mechanism around each second coil end and against the second enlarged tip; and
means for releasing the first and second attaching means from said first and second coil ends thereby allowing the tubular stent to expand from the restrained stent diameter to the expanded stent diameter to contact the wall of the body lumen.

14. A system for implanting a tubular stent at a site in a body lumen at an expanded stent diameter and stent length in contact with the wall of the body lumen comprising:

a stent having a substantially tubular shape and an expanded stent length and expanded stent diameter in an expanded state formed of a plurality of coils each having a pre-determined coil cross-section and extending for a predetermined length between a first coil end and a second coil end and each wound in a common winding direction and having a common winding pitch through a substantial portion of the coil length intermediate the first and second coil ends, and with first end coupling means for coupling the plurality of first coil ends together at a first stent end for cooperatively maintaining said plurality of coils in an interleaved, multi-filar winding relationship providing the substantially tubular stent shape and maintaining substantially equal coil spacing between adjacent turns of the plurality of coils through a substantial portion of the lengths of the plurality of coils, said first end coupling means comprising a first enlarged tip coupled to said common junction having a cross-section exceeding, in at least one direction, the combined cross-section of the plurality of coils attached together at the first stent end, and a second enlarged tip attached to each of the second coil ends, whereby the first coil ends are commonly coupled together and the second coil ends are separated from one another; and a stent implantation catheter extending between proximal and distal ends and having a stent mounting and release mechanism for restraining said tubular stent wound around a distal end segment thereof and reduced to a reduced state stent diameter and stent length, said stent mounting and release mechanism further comprising:
first means for attaching the stent implantation catheter release mechanism around the first coil end and against the first enlarged tip;
second means for attaching the stent implantation catheter release mechanism around the second coil ends and against each second enlarged tip; and
means for releasing said first and second attaching means from said first and second coil ends thereby allowing the tubular stent to expand from the restrained stent diameter to the expanded stent diameter to contact the wall of the body lumen.

15. The system of claim 14, wherein said plurality of coils of said coil stent are formed with a rectangular cross-section, and said stent mounting and release mechanism for restraining said tubular stent wound around a distal end segment thereof and reduced to a reduced state stent diameter and stent length further comprises:
means for restraining each coil turn of said plurality of coils wound over the adjacent coil along the length of said catheter distal end segment to stack said plurality of coils over one another and to shorten the restrained stent length to approximately the expanded stent length.

16. The system of any of claims 13–14, wherein said plurality of coils of said coil stent are formed with a rectangular cross-section.

17. The system of any of claims 13–14, wherein said coils of said coil stent have an elasticity allowing said coils to be wound under applied force to a restrained diameter on stent deployment means to allow for introduction of said coil stent to the site of implantation while reduced in diameter and to unwind from said restrained diameter and to resume substantially said expanded stent diameter when implanted at the site.

18. The system of any of claims 13–15, wherein multi-filar coil stent of any of claims 1–8, wherein said coils of said coil stent are formed of a superelastic metal alloy and have an elasticity allowing said coils to be wound under applied force to a restrained diameter of about 10% to 90% of the expanded stent diameter on stent deployment means to allow for introduction of said coil stent to the site of implantation while reduced in diameter and to unwind from said restrained diameter and to resume substantially said expanded stent diameter when implanted at the site.

19. The system of any of claims 13–15, wherein said coils of said coil stent have an elasticity allowing said coils to be wound under applied force to a restrained diameter and a restrained pitch on stent deployment means to allow for introduction of said coil stent to the site of implantation while reduced in diameter and having a reduced state stent length that is substantially the same as the expanded stent length and to unwind from said restrained diameter and to resume substantially said expanded stent diameter, pitch and stent length when implanted at the site.

20. The system of any of claims 13–15, wherein said plurality of coils have a common cross-section and said plurality of coils comprise two coils.

21. The system of any of claims 13–15, wherein, wherein said plurality of coils have a common cross-section and said plurality of coils comprise three coils.

22. The system of any of claims 13–15, wherein said coils of said coil stent are formed of a superelastic metal alloy and have an elasticity allowing said coils to be wound under applied force to a restrained diameter and a restrained pitch on stent deployment means to allow for introduction of said coil stent to the site of implantation while reduced in diameter and having a reduced state stent length that is substantially the same as the expanded stent length and to unwind from said restrained diameter and to resume substantially said expanded stent diameter, pitch and stent length when implanted at the site.

23. The system of any of claims 13–15, further comprising: a tubular sheath of fluid pervious or impervious material fitted over said plurality of coils.

24. A method of implanting a tubular stent at a site in a body lumen at an expanded stent diameter and stent length in contact with the wall of the body lumen comprising the steps of:
providing a stent having a substantially tubular shape and an expanded stent length and expanded stent diameter in an expanded state formed of a plurality of coils each having a pre-determined coil cross-section and extending for a predetermined length between a first coil end and a second coil end and each wound in a common winding direction and having a common winding pitch through a substantial portion of the coil length intermediate the first and second coil ends, and with first end coupling means for coupling the plurality of first coil ends together at a first stent end and with second end coupling means for coupling the plurality of second coil ends together at a second stent end for cooperatively maintaining said plurality of coils in an interleaved, multi-filar winding relationship providing the substantially tubular stent shape and maintaining substantially equal coil spacing between adjacent turns of the plurality of coils through a substantial portion of the lengths of the plurality of coils, said first end coupling means comprising a first enlarged tip attached to each of the first coil ends having a cross-section exceeding, in at least one direction, the combined cross-section of the plurality of coils attached together at the first stent end, and said second end coupling means comprising a second enlarged tip attached to each of the second coil ends, whereby the first coil ends are commonly coupled together and the second coil ends are commonly coupled together;
providing a stent implantation catheter extending between proximal and distal ends and having a stent mounting and release mechanism for restraining said tubular stent reduced to a reduced state stent diameter and stent length along a distal end segment thereof;
attaching the stent implantation catheter release mechanism around each first coil end and against the first enlarged tip;
winding the adjacent turns of the plurality of coils around the distal end segment at the restrained stent diameter to mount the stent in a restrained state having a restrained stent length to the catheter distal end segment;
attaching the stent implantation catheter release mechanism around each second coil end and against the second enlarged tip;
introducing the stent wound onto the catheter distal end segment in the restrained state to the implantation site; and operating the stent implantation catheter release mechanism to release the first and second coil ends thereby allowing the tubular stent to expand from the restrained stent diameter to the expanded stent diameter to contact the wall of the body lumen.

25. The method of claim 24, wherein said winding step further comprises the step of:

winding each coil turn of said plurality of coils along the length of said catheter distal end segment so that the restrained stent length is approximately equal to the expanded stent length.

26. A method of implanting a tubular stent at a site in a body lumen at an expanded stent diameter and stent length in contact with the wall of the body lumen comprising the steps of:

providing a stent having a substantially tubular shape and an expanded stent length and expanded stent diameter in an expanded state formed of a plurality of coils each having a pre-determined coil cross-section and extending for a predetermined length between a first coil end and a second coil end and each wound in a common winding direction and having a common winding pitch through a substantial portion of the coil length intermediate the first and second coil ends, and with first end coupling means for coupling the plurality of first coil ends together at a first stent end for cooperatively maintaining said plurality of coils in an interleaved, multi-filar winding relationship providing the substantially tubular stent shape and maintaining substantially equal coil spacing between adjacent turns of the plurality of coils through a substantial portion of the lengths of the plurality of coils, said first end coupling means comprising a first enlarged tip coupled to said common junction having a cross-section exceeding, in at least one direction, the combined cross-section of the plurality of coils attached together at the first stent end, and a second enlarged tip attached to each of the second coil ends, whereby the first coil ends are commonly coupled together and the second coil ends are separated from one another;

providing a stent implantation catheter extending between proximal and distal ends and having a stent mounting and release mechanism for restraining said tubular stent reduced to a reduced state stent diameter and stent length along a distal end segment thereof;

attaching the stent implantation catheter release mechanism around the first coil end and against the first enlarged tip;

winding the adjacent turns of the plurality of coils around the distal end segment at the restrained stent diameter to mount the stent in a restrained state to the catheter distal end segment;

attaching the stent implantation catheter release mechanism around the second coil ends adjacent each respective second enlarged tip;

introducing the stent wound onto the catheter distal end segment in the restrained state to the implantation site; and operating the stent implantation catheter release mechanism to release the first and second coil ends thereby allowing the tubular stent to expand from the restrained stent diameter to the expanded stent diameter to contact the wall of the body lumen.

27. The method of claim 26, wherein said plurality of coils of said coil stent are formed with a rectangular cross-section, and said winding step further comprises the step of:

winding each coil turn of said plurality of coils over the adjacent coil along the length of said catheter distal end segment to stack said plurality of coils over one another and to shorten the restrained stent length to approximately the expanded stent length.

* * * * *